United States Patent

Ando et al.

Patent Number: 5,384,320
Date of Patent: Jan. 24, 1995

[54] N-HYDROXYUREA DERIVATIVES WHICH INHIBIT LIPOXYGENASE

[75] Inventors: Kazuo Ando, Taketoyo; Takafumi Ikeda, Handa, both of Japan

[73] Assignee: Pfizer Inc, New York, N.Y.

[21] Appl. No.: 162,104

[22] Filed: Dec. 10, 1993

[30] Foreign Application Priority Data

Jun. 13, 1991 [JP] Japan .................. 3-142123

[51] Int. Cl.⁶ .................. A61K 31/535; A61K 31/40; C07D 295/155
[52] U.S. Cl. .................. 514/231.2; 514/429; 544/168; 548/577
[58] Field of Search .................. 544/168; 548/577; 514/231.2, 429

[56] References Cited

U.S. PATENT DOCUMENTS 4,981,865 1/1991 Belliotti et al. .................. 514/480

FOREIGN PATENT DOCUMENTS 196184 10/1986 European Pat. Off. .
292699 11/1988 European Pat. Off. .
374602 6/1990 European Pat. Off. .

OTHER PUBLICATIONS

T. A. Hicks et al., *J. Med. Chem.*, 22, No. 12, 1460–1464 (Dec. 1979).

*Primary Examiner*—Robert W. Ramsuer
*Attorney, Agent, or Firm*—Peter C. Richardson; Gregg C. Benson; Mervin E. Brokke

[57] ABSTRACT

Compounds of the formula

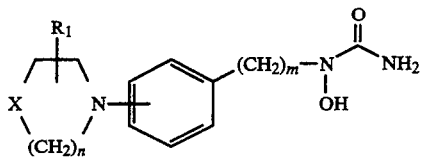

wherein X is $-CH_2-$, $-O-$ or $-S-$, m is 1 to 3, n is 1 or 2 and $R_1$ is hydrogen, $C_1$ to $C_4$ alkyl, aryl or aryl substituted with one or more substituents selected independently from the group consisting of halogen, nitro, cyano, $C_1$ to $C_{10}$ alkyl, $C_1$ to $C_{10}$ halosubstituted alkyl, $C_1$ to $C_6$ alkoxy, alkoxycarbonyl having from one to ten carbon atoms in the alkoxy moiety, aminocarbonyl, alkylaminocarbonyl having from one to ten carbon atoms in the alkyl moiety and dialkylaminocarbonyl having from one to ten carbon atoms in each of the alkyl moieties, and the pharmaceutically acceptable salts thereof, inhibit the enzyme lipoxygenase and are useful in treating allergy and inflammatory and cardiovascular conditions for which the action of lipoxygenase has been implicated. These compounds form the active ingredient in pharmaceutical compositions for treating such conditions.

14 Claims, No Drawings

N-HYDROXYUREA DERIVATIVES WHICH INHIBIT LIPOXYGENASE

BACKGROUND OF THE INVENTION

FIELD OF THE INVENTION

This invention relates to novel azacyclic-substituted phenyl N-hydroxyurea derivatives. The compounds of the present invention inhibit the action of the enzyme lipoxygenase and are useful in the treatment or alleviation of inflammatory diseases, allergy and cardiovascular diseases in mammals. This invention also relates to pharmaceutical compositions comprising such compounds and to the use of such compounds in treating inflammatory diseases, allergy and cardiovascular diseases in mammals. This invention further relates to methods of making such compounds.

Arachidonic acid is known to be the biological precursor of several groups of endogenous metabolites, prostaglandins including prostacyclins, thromboxanes and leukotrienes. The first step of arachidonic acid metabolism is the release of arachidonic acid and related unsaturated fatty acids from membrane phospholipids, via the action of phospholipase. Free fatty acids are then metabolized either by cyclooxygenase to produce the prostaglandins and thromboxanes or by lipoxygenase to generate hydroperoxy fatty acids which may be further converted to the leukotrienes. Leukotrienes have been implicated in the pathophysiology of inflammatory diseases, including rheumatoid arthritis, gout, asthma, ischemia reperfusion injury, psoriasis and inflammatory bowel disease. Any drug that inhibits lipoxygenase is expected to provide significant new therapy for both acute and chronic inflammatory conditions.

Several review articles on lipoxygenase inhibitors have been reported (See H. Masamune et al., Ann. Rep. Med. Chem., 24, 71–80 (1989) and B. J. Fitzsimmons et al., Leukotrienes and Lipoxygenases, 427–502 (1989).

Compounds of the same general class as the compounds of the present invention are disclosed in EP 279263 A2, EP 196184 A2, JP 502179/88 and U.S. Pat. No. 4,822,809.

SUMMARY OF THE INVENTION

The present invention provides novel N-hydroxyurea derivatives of the following formula and their pharmaceutically acceptable salts:

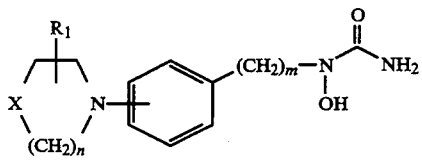

wherein X is —$CH_2$—, —O— or —S—; m is 1 to 3; n is 1 or 2; and $R_1$ is hydrogen, $C_1$ to $C_4$ alkyl, aryl or aryl substituted with one or more substituents independently selected from the group consisting of halogen, nitro, cyano, $C_1$ to $C_{10}$ alkyl, $C_1$ to $C_{10}$ halosubstituted alkyl, $C_1$ to $C_6$ alkoxy, alkoxycarbonyl having from one to ten carbon atoms in the alkoxy moiety, aminocarbonyl, alkylaminocarbonyl having from one to ten carbon atoms in the alkyl moiety and dialkylaminocarbonyl having from one to ten carbon atoms in each of the alkyl moieties. The substituent $R_1$ may be substituted at any available position on the azacyclic ring and, similarly, the azacyclic ring may attach to the central phenyl group at any available position.

This invention also concerns pharmaceutical compositions comprising a pharmaceutically acceptable carrier or diluent and a compound of the invention or a pharmaceutically acceptable salt thereof. This invention further concerns methods of treating inflammatory diseases, allergy and cardiovascular diseases in mammals comprising administration of such compounds or compositions.

DETAILED DESCRIPTION OF THE INVENTION

Definitions

"Halo" and "halogen" mean radicals derived from the elements fluorine, chlorine, bromine and iodine.

"Alkyl" means straight or branched saturated hydrocarbon radicals, for example, methyl, ethyl, n-propyl and isopropyl.

"Alkoxy" means —$OR^2$ wherein $R^2$ is an alkyl radical, for example, methoxy, ethoxy, propoxy, isopropoxy and butoxy.

"Alkoxycarbonyl" means —$C(=O)R^3$ wherein $R^3$ is an alkoxy radical, for example, methoxycarbonyl, ethoxycarbonyl and propoxycarbonyl.

"Alkylaminocarbonyl" means —$C(=O)NHR^4$ wherein $R^4$ is an alkyl radical, for example, methylaminocarbonyl, ethylaminocarbonyl and propylaminocarbonyl.

"Dialkylaminocarbonyl" means —$C(=O)NR^5R^6$ wherein $R^5$ and $R^6$ are independently alkyl radicals, for example, dimethylaminocarbonyl, diethylaminocarbonyl and methylethylaminocarbonyl.

"Aryl" means aromatic radicals, for example, phenyl, naphthyl, pyridyl, quinolyl, thienyl, furyl and phenoxyphenyl.

"Halosubstituted alkyl" refers to an alkyl radical as described above substituted with one or more halogens, for example, chloromethyl, trifluoromethyl and 2,2,2-trichloroethyl.

Some of the compounds of the above formula may form acid salts. The pharmaceutically acceptable acid salts are those formed from acids which form non-toxic acid salts, for example, hydrochloride, hydrobromide, sulfate or bisulfate, phosphate or acid phosphate, acetate, citrate, fumarate, gluconate, lactate, maleate, succinate, tartrate, methansulfonate, benzensulfonate, toluene-sulfonate, and formate salts.

This invention includes pharmaceutical compositions for treatment of inflammatory diseases, allergy and cardiovascular diseases in a mammal which comprises a pharmaceutically acceptable carrier or diluent and a compound of the above formula or a pharmaceutically acceptable salt thereof.

This invention also includes pharmaceutical compositions for inhibiting the action of lipoxgenase enzyme in a mammal which comprises a pharmaceutically acceptable carrier and a compound of the above formula or a pharmaceutically acceptable salt thereof.

The novel compounds of this invention may be prepared as shown in the reaction scheme described below.

GENERAL SYNTHETIC SCHEME

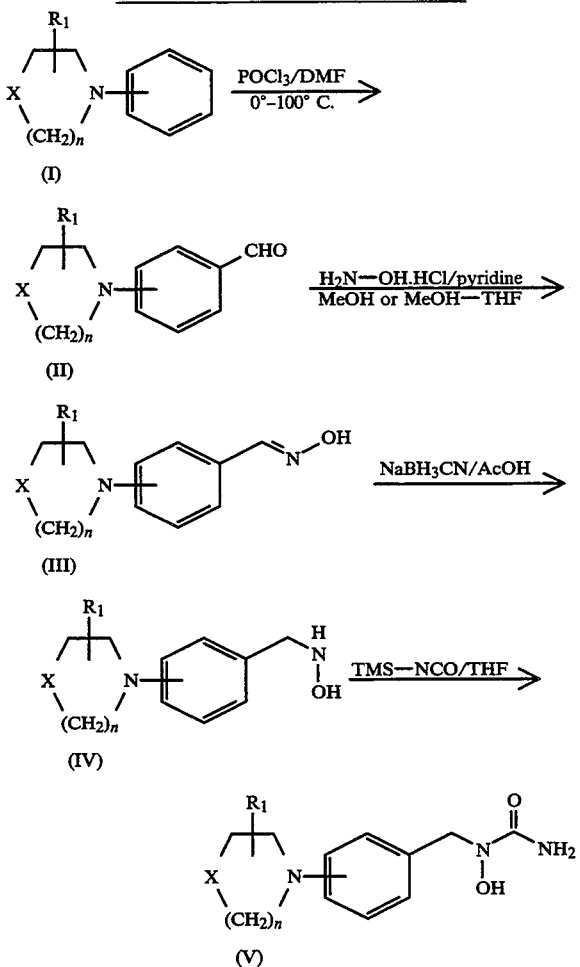

The compounds of the invention may be prepared by a number of synthetic methods. Except where otherwise indicated, in the above reaction scheme and discussion that follow, $R_1$, X and n are as previously defined.

In one embodiment, the compounds of the invention (V) are prepared according to the reaction steps outlined below.

The starting materials used in the procedure of the above reaction scheme may be prepared from commercially available compounds or known compounds according to standard methods known in the art.

In the first step, aldehyde derivatives (II) are easily prepared from the corresponding phenyl derivatives (I) by standard methods known in the art (Vilsmeier reaction). For example, the phenyl (I) is reacted with N,N-dimethylformamide (DMF) and phosphorus oxychloride in a reaction-inert solvent. A suitable solvent is dichloromethane, however, DMF in large excess can be utilized in this process. Generally, the reaction is run for several minutes to about 24 hours. The reaction temperature may range from about 0° C. to about 100° C. The product can be isolated and purified by conventional procedures, such as recrystallization or chromatography.

In the second step, the aldehyde (II) is treated with hydroxylamine hydrochloride to afford the oxime (III). This reaction is carried out in a reaction-inert solvent in the presence of suitable base such a pyridine or triethylamine usually at room temperature. Suitable solvents which do not react with reactants and/or products are for example, methanol, ethanol and mixtures thereof. The oxime (III) thus obtained is isolated by standard methods. Without further purification, in the next step, the oxime (III) is converted to the requisite hydroxylamine (IV) with a suitable reducing agent (for example, see R. F. Borch et al, J. Am. Chem. Soc., 93, 2897 (1971)). Reducing agents of choice include, but are not limited to, sodium cyanoborohydride and borane-complexes such as boron-pyridine, borontriethylamine and boron-dimethylsulfide, however, triethylsilane in trifluoroacetic acid may also be employed.

The aforementioned hydroxylamine (IV) is easily prepared by standard synthetic procedures from readily available carbonyl compounds, i.e., ketone, aldehyde, alcohol or halogen compounds (for example, see R. L. Danheiser et al., Tetrahedron Lett., 28, 3299 (1987), M. Kolobielski et al., J. Am. Chem. Soc., 79, 5820 (1957), Y. Kobayashi et al., J. Org. Chem., 47, 3232 (1982) and Fieser et al., J. Am. Chem. Soc., 70, 3147 (1948)).

Alternatively the hydroxylamine (IV) can be prepared by treating the corresponding alcohol with N,O-bis(tert-butyloxycarbonyl)hydroxylamine under Mitsunobu-type reaction conditions followed by acid catalyzed hydrolysis of the N,O-protected intermediate product (see JP (Kokai) 45344/89).

The aforementioned hydroxylamine (IV) may also be prepared from a suitable halide compound by the reaction with O-protected hydroxylamine and subsequent deprotecton (see W. P. Jackson et al., J. Med. Chem., 31, 499, (1988)). Preferred O-protected hydroxylamines include, but are not limited to O-tetrahydropyranyl-, O-trimethylsilyl-and O-benzylhydroxylamine.

The hydroxylamine of formula (IV) thus obtained by the above mentioned representative procedures is isolated by standard methods and purification can be achieved by conventional means, such as recrystallization and chromatography.

In the last step, the hydroxylamine (IV) is treated with trimethylsilylisocyanate in a reaction-inert solvent usually at ambient through to reflux temperature. Suitable solvents which do not react with reactants and/or products include, for example, tetrahydrofuran, dioxane, methylene chloride and benzene. An alternative procedure employs treatment of the hydroxylamine (IV) with gaseous hydrogen chloride in a reaction-inert solvent such as benzene or toluene and then subsequent treatment with phosgene. Reaction temperatures are usually in the range of ambient temperature through to boiling point of solvent. The intermediate carbamoyl chloride is not isolated but subjected to (i.e. in situ) reaction with aqueous ammonia. The urea compound (V) thus obtained is isolated by conventional means, such as recrystallization and chromatography.

The pharmaceutically acceptable salts of the novel compounds of the present invention are readily prepared by contacting said compounds with a stoichiometric amount of, in the case of a non-toxic cation, an appropriate metal hydroxide or alkoxide or amine in either aqueous solution or a suitable organic solvent, or, in the case of a non-toxic acid salt, an appropriate mineral or organic acid in either aqueous solution or a suitable organic solvent. The salt may then be obtained by precipitation or by evaporation of the solvent.

The compounds of this invention inhibit the activity of the enzyme lipoxygenase. This inhibition has been demonstrated by an assay using rat peritoneal cavity resident cells which determines the effect of said compounds on the metabolism of arachidonic acid.

The compounds of Examples 1 to 3 were tested according to the methods described in "Synthesis of leukotrienes by peritoneal macrophages," *Jap. J. Inflammation*, 7, 145-150 (1987), and were shown to be lipoxygenase inhibitors, exhibiting $IC_{50}$ values in the range of about 0.33 to about 30 $\mu M$, for lipoxygenase inhibition.

The ability of the compounds of the present invention to inhibit lipoxygenase makes them useful for controlling the symptoms induced by the endogenous metabolites arising from arachidonic acid in a mammalian subject. The compounds are therefore valuable in the prevention and treatment of such disease states in which the accumulation of arachidonic acid metabolites is the causative factor, e.g., allergic bronchial asthma, skin disorders, rheumatoid arthritis, osteoarthritis and thrombosis.

The compounds of the formula and their pharmaceutically acceptable salts are of particular use in the prevention and treatment of inflammatory diseases, allergy and cardiovascular diseases in a human subject.

Methods of Administration

For treatment of the various conditions described above, the compounds of the invention and their pharmaceutically acceptable salts can be administered to a human subject either alone or, preferably, in combination with pharmaceutically acceptable carriers or diluents in a pharmaceutical composition, according to standard pharmaceutical practice. A compound can be administered via a variety of conventional routes of administration including orally, parenterally and by inhalation. When the compounds are administered orally, the dose range will generally be from about 0.1 to about 20 mg/kg/day, based on the body weight of the subject to be treated, preferably from about 0.1 to about 1.0 mg/kg/day in single or divided doses. If parenteral administration is desired, then an effective dose will generally be from about 0.1 to about 1.0 mg/kg/day. In some instances it may be necessary to use dosages outside these limits, since the dosage will necessarily vary according to the age, weight and response of the individual patient as well as the severity of the patient's symptoms and the potency of the particular compound being administered.

For oral administration, the compounds of the invention and their pharmaceutically acceptable salts can be administered, for example, in the form of tablets, powders, lozenges, syrups or capsules, or as an aqueous solution or suspension. In the case of tablets for oral use, carriers which are commonly used include lactose and corn starch. Lubricating agents, such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added.

For intramuscular, intraperitoneal, subcutaneous and intravenous use, a sterile solution of the active ingredient is usually prepared, and the pH of the solutions should be suitably adjusted and buffered. For intravenous use, the total concentration of solute should be controlled to make the preparation isotonic.

EXAMPLES

The present invention is illustrated by the following examples. However, it should be understood that the invention is not limited to specific details of these examples.

Proton nuclear magnetic resonance (NMR) spectra were measured at 270 MHz unless otherwise indicated and peak positions are expressed in parts per million (ppm) downfield from tetramethylsilane. The peak shapes are denoted as follows: s, singlet; d, doublet; t, triplet; q, quartet; m, multiplet; br, broad.

Example 1 N-Hydroxy-N-[4-(1-pyrrolidyl)benzyl]urea

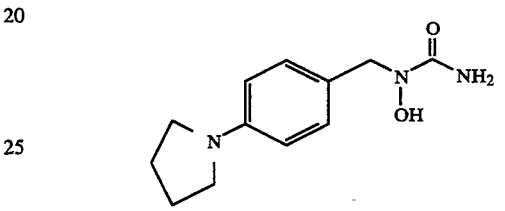

The title compound was prepared according to the following synthetic scheme.

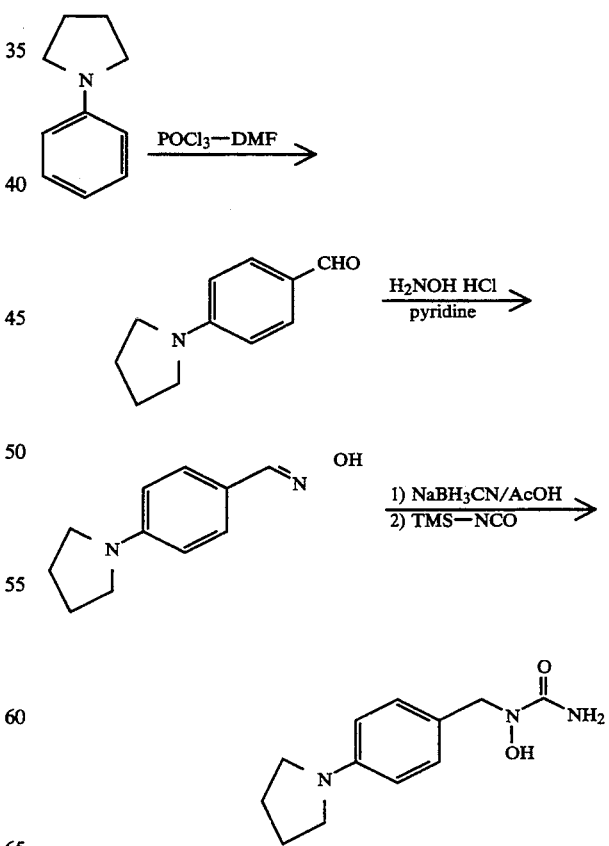

Step 1, 1-(4-formylphenyl)pyrrolidine

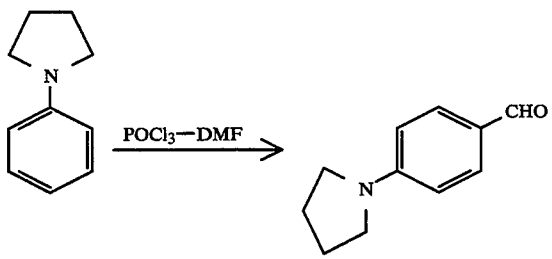

POCl₃ (6.13 g) was added to stirred DMF (7 ml) at 0° C. and the mixture was stirred for 30 minutes at room temperature. The mixture was added dropwise to a solution of 1-phenylpyrrolidine (5.0 g) in DMF (30 ml) at 0° C. and the resulting solution was stirred overnight at room temperature. The reaction mixture was poured into an ice water mixture and extracted with Et₂O. The Et₂O layer was washed with saturated NaCl solution, dried over MgSO₄ and the solution was concentrated in vacuo. The resulting crystalline mass was washed with Et₂O-hexane, yielding 1-(4-formylphenyl)pyrrolidine (3.28 g).

Step 2, N-hydroxy-N-[4-(1-pyrrolidyl)benzyl]urea

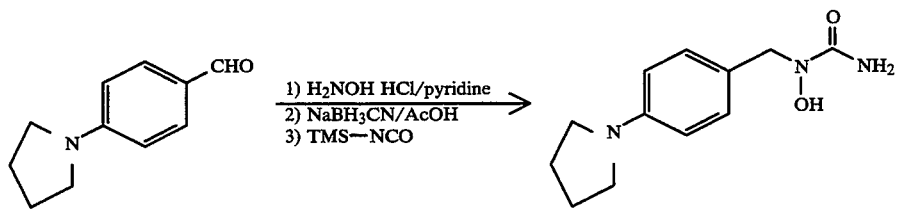

To a stirred solution of 1-(4-formylphenyl)pyrrolidine (1.5 g) in MeOH (50 ml) was added hydroxylamine hydrochloride (0.62 g) and pyridine (0.70 g). The mixture was stirred for 2 hours at room temperature and the solvent was removed under reduced pressure. The resulting crystals were washed with Et₂O. Without further purification, a stirred solution of the product (1.03 g) in acetic acid (20 ml) was treated with NaBH₃CN (0.34 g) by portions at room temperature. The mixture was stirred for 3 hours then H₂O was added. The reaction mixture was cooled to 0° C. and aqueous NaOH solution was added until the mixture was basic. The resulting mixture was extracted with CH₂Cl₂ and washed with saturated NaCl solution. The extract was dried over MgSO₄ and concentrated in vacuo. Without further purification, the crude product (1.01 g) was dissolved in dry THF (22 ml). The THF solution was stirred and trimethylsilylisocyanate (1.5 ml) was added at room temperature. The mixture was stirred for 1 hour and the solvent was removed under reduced pressure. The precipitate was purified by recrystallization from EtOH, yielding the title compound (0.40 g), m.p. 127.5°-128° C. (dec.).

IR (KBr) cm⁻¹: 3465, 1645, 1625, 1530, 785. NMR (DMSO-d6) δ: 9.15 (s, 1H), 7.08 (d, J=8.6 Hz, 2H), 6.47 (d, J=8.6 Hz, 2H), 6.22 (s, 2H), 4.36 (s, 2H), 3.19 (dd, J=6.6, 6.6 Hz, 4H), 1.94 (dd, J=6.6, 6.6 Hz, 4H).

Example 2
N-Hydroxy-N-[4-(morpholin-4-yl)benzyl]urea

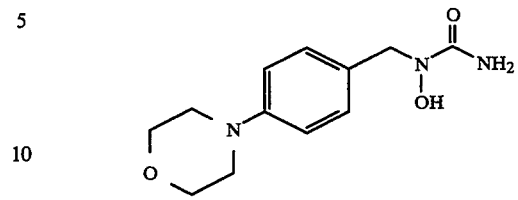

The title compound, m.p. 151°-152° C. (dec.), was prepared according to the procedure of Example 1 from 1-phenylmorpholine.

IR (KBr) cm⁻¹: 3480, 1660, 1640, 1520, 1455, 923, 786. NMR (DMSO-d6) δ: 9.22 (s, 1H), 7.14 (d, J=8.6 Hz, 2H), 6.88 (d, J=8.6 Hz, 2H), 6.26 (s, 2H), 4.40 (s, 2H), 3.73 (dd, J=4.8, 4.8 Hz, 4H), 3.06 (dd, J=4.8, 4.8 Hz, 4H).

Example 3
N-Hydroxy-N-[4-(2-phenylpyrrolidin-1-yl)benzyl]urea

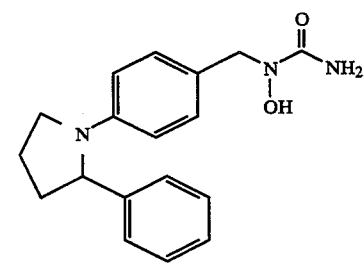

The title compound, m.p. 141.5°-143° C. (dec.), was prepared according to the procedure of Example 1 from 1,2-diphenylpyrrolidine.

IR (KBr) cm₋₁: 3550, 3395, 1649, 1615, 1560, 1520, 700.

NMR (DMSO-d6) δ: 9.11 (s, 1H), 7.26-7.32 (m, 2H), 7.16-7.22 (m, 3H), 6.99 (d, J=8.8 Hz, 2H), 6.36 (d, J=8.8 Hz, 2H), 6.18 (br s, 2H), 4.71 (dd, J=8.1, 2.2 Hz, 1H), 4.31 (s, 2H), 3.64-3.71 (m, 1H), 3.29-3.37 (1H), 2.33-2.41 (m, 1H), 1.91-1.99 (m, 2H), 1.76-1.83 (m, 1H).

We claim:
1. A compound of the formula

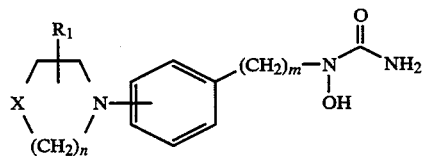

and the pharmaceutically acceptable salts thereof, wherein:

X is —CH$_2$—, —O— or —S—;

m is 1 to 3;

n is 1 or 2; and

R$_1$ is hydrogen, C$_1$ to C$_4$ alkyl, aryl or aryl substituted with one or more substituents selected independently from the group consisting of halogen, nitro, cyano, C$_1$ to C$_{10}$ alkyl, C$_1$ to C$_{10}$ halosubstituted alkyl, C$_1$ to C$_6$ alkoxy, alkoxycarbonyl having from one to ten carbon atoms in the alkoxy moiety, aminocarbonyl, alkylaminocarbonyl having from one to ten carbon atoms in the alkyl moiety and dialkylaminocarbonyl having from one to ten carbon atoms in each of the alkyl moieties.

2. A compound according to claim 1 wherein X is —CH$_2$—.

3. A compound according to claim 1 wherein X is —O—.

4. A compound according to claim 2 wherein R$_1$ is hydrogen.

5. A compound according to claim 2 wherein R$_1$ is aryl or substituted aryl.

6. A compound according to claim 5 wherein R$_1$ is phenyl.

7. A compound according to claim 3 wherein R$_1$ is hydrogen.

8. A compound according to claim 3 wherein R$_1$ is aryl or substituted aryl.

9. A compound according to claim 4 which is N-hydroxy-N-[4-(1-pyrrolidyl)benzyl]urea.

10. A compound according to claim 6 which is N-hydroxy-N-[4-(2-phenylpyrrolidin-1-yl)benzyl]urea.

11. A compound according to claim 7 which is N-hydroxy-N-[4-(morpholin-4-yl)benzyl]urea.

12. A pharmaceutical composition for the treatment of allergic, inflammatory or cardiovascular conditions in a mammal comprising a therapeutically effective amount of a compound of claim 1 or a pharmaceutically acceptable salt thereof together with a pharmaceutically acceptable carrier.

13. A method of inhibiting lipoxygenase in a mammal comprising administering to said mammal a lipoxygenase-inhibiting amount of a compound according to claim 1 or a pharmaceutically acceptable salt thereof.

14. A method of treating allergy or inflammatory or cardiovascular conditions in a mammal comprising administering to said mammal a lipoxygenase-inhibiting amount of a compound according to claim 1 or a pharmaceutically acceptable salt thereof.

* * * * *